United States Patent [19]

Chess et al.

[11] Patent Number: 5,051,260

[45] Date of Patent: Sep. 24, 1991

[54] METHOD AND COMPOSITION FOR ENHANCING THE CUTANEOUS PENETRATION OF PHARMACOLOGICALLY ACTIVE AGENTS

[75] Inventors: Samuel Chess, Newport Beach; Jerry L. McCullough; Gerald D. Weinstein, both of Irvine, all of Calif.

[73] Assignee: The Regents of the University of California, Alameda, Calif.

[21] Appl. No.: 556,982

[22] Filed: Sep. 20, 1990

Related U.S. Application Data

[60] Division of Ser. No. 408,757, Sep. 18, 1989, Pat. No. 4,971,800, which is a continuation-in-part of Ser. No. 216,804, Jul. 8, 1988, abandoned, which is a continuation-in-part of Ser. No. 74,262, Jul. 16, 1987, abandoned.

[51] Int. Cl.⁵ .......................... A61K 9/32; A61K 9/70; A61K 7/48
[52] U.S. Cl. ..................................... 424/449; 514/847; 514/969
[58] Field of Search ................ 424/401, 449; 514/847, 514/969

[56] References Cited

U.S. PATENT DOCUMENTS

| | | | |
|---|---|---|---|
| 2,266,777 | 12/1941 | Lieser | 536/32 |
| 2,282,827 | 5/1942 | Rothrock | 106/252 |
| 2,284,637 | 6/1942 | Catlin | 528/49 |
| 2,284,896 | 6/1942 | Hanford et al. | 525/61 |
| 2,511,544 | 6/1950 | Rinke et al. | 528/85 |
| 2,729,618 | 1/1956 | Muller et al. | 525/440 |
| 2,814,605 | 11/1957 | Stillmar | 525/458 |
| 2,858,298 | 10/1958 | Burt | 528/76 |
| 2,871,226 | 1/1959 | McShane | 528/65 |
| 2,915,496 | 12/1959 | Swart et al. | 524/710 |
| 2,948,691 | 8/1960 | Windemuth et al. | 521/174 |
| 3,049,514 | 8/1962 | Damusis | 528/60 |
| 3,049,515 | 8/1962 | Damusis | 528/77 |
| 3,049,516 | 8/1962 | Damusis | 528/60 |
| 3,472,931 | 10/1969 | Stoughton | 514/50 |
| 3,477,977 | 11/1969 | Schnell et al. | 106/252 |
| 3,539,482 | 11/1970 | Stewart | 524/591 |
| 3,551,554 | 12/1970 | Herschler | 426/7.1 |
| 3,594,409 | 7/1971 | Lachampt et al. | 560/198 |
| 3,797,494 | 3/1974 | Zaffaroni | 424/434 |
| 3,822,238 | 7/1974 | Blair et al. | 528/59 |
| 3,867,528 | 2/1975 | Ritter et al. | 514/174 |
| 3,968,245 | 7/1976 | Higuchi | 514/653 |
| 3,975,350 | 8/1976 | Hudgin et al. | 524/108 |
| 3,989,816 | 11/1976 | Rajadhyaksha | 424/60 |
| 4,006,218 | 2/1977 | Sipos | 424/54 |
| 4,039,664 | 8/1977 | Stoughton et al. | 514/462 |
| 4,060,084 | 11/1977 | Chandresekaran et al. | 424/448 |
| 4,079,028 | 3/1978 | Emmons et al. | 524/507 |

(List continued on next page.)

FOREIGN PATENT DOCUMENTS 2557576 7/1985 France .
1179231 1/1970 United Kingdom .

OTHER PUBLICATIONS

Franz. *J. Invest. Dermatol.* 64:190-195 (1975).
"The Finite Dose Technique as a Valid In Vitro Model for the Study of Percutaneous Absorption in Man", in *Current Problems in Dermatology*, vol. 7, pp. 58-68, Ed. J. W. H. Mali (Karger, Basel, 1978).
Kambic et al., C & EN, "Biomaterials in Artificial Organs", 4/14/86, pp. 31-48.
Saunders et al., *Polyurethanes: Chemistry, and Technology*, Part I (Chemistry), 1942 (Interscience Publication), pp. 63-128.

*Primary Examiner*—Thurman Page
*Assistant Examiner*—Carlos Azpuru
*Attorney, Agent, or Firm*—Majestic, Parsons, Siebert & Hsue

[57] ABSTRACT

Method and compositions for enhancing the cutaneous penetration of topically or transdermally delivered pharmacologically active agents. The compositions include various urethane compounds as permeation enhancers, the urethane compounds formed from reaction of a monomeric organic diisocyanate with a hydroxy- or hydroxy/alkoxy-terminated linear alkylene or polyalkylene glycol or polyether.

8 Claims, 4 Drawing Sheets

IN VITRO PENETRATION OF METHOTREXATE WITH URETHANE COMPOUNDS VS AZONE

U.S. PATENT DOCUMENTS

| Patent No. | Date | Inventor | Class |
|---|---|---|---|
| 4,130,667 | 12/1978 | Smith et al. | 514/777 |
| 4,155,892 | 5/1979 | Emmons et al. | 524/507 |
| 4,245,110 | 1/1981 | Engelhard et al. | 560/160 |
| 4,246,261 | 1/1981 | Van Scott et al. | 514/171 |
| 4,287,214 | 9/1981 | Van Scott et al. | 514/732 |
| 4,316,893 | 2/1982 | Rajadhyaksha | 514/24 |
| 4,405,616 | 9/1983 | Rajadhyaksha | 514/788 |
| 4,424,234 | 1/1984 | Alderson et al. | 514/558 |
| 4,440,777 | 1/1984 | Zupan | 514/420 |
| 4,483,759 | 11/1984 | Szycher et al. | 522/20 |
| 4,523,005 | 6/1985 | Szycher et al. | 528/76 |
| 4,543,405 | 9/1985 | Ambrose et al. | 528/78 |
| 4,568,343 | 2/1986 | Leeper et al. | 424/447 |
| 4,614,787 | 9/1986 | Szycher et al. | 528/75 |
| 4,638,043 | 1/1987 | Szycher et al. | 528/75 |
| 4,710,497 | 12/1987 | Heller et al. | 514/221 |
| 4,731,241 | 3/1988 | Yamada et al. | 514/236.2 |
| 4,732,892 | 3/1988 | Sarpotdar et al. | 514/178 |
| 4,746,675 | 5/1988 | Makino et al. | 514/423 |
| 4,863,738 | 9/1989 | Taskovich | 424/449 |
| 4,885,174 | 12/1989 | Bodor et al. | 424/449 |

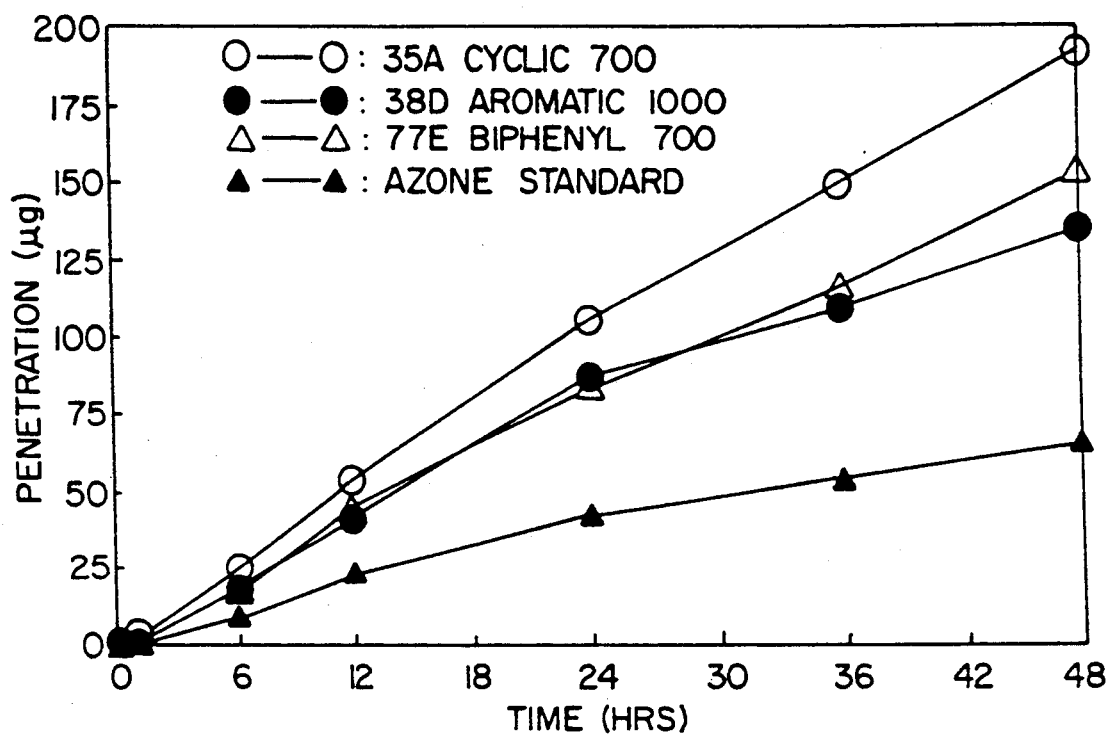
FIG._1.
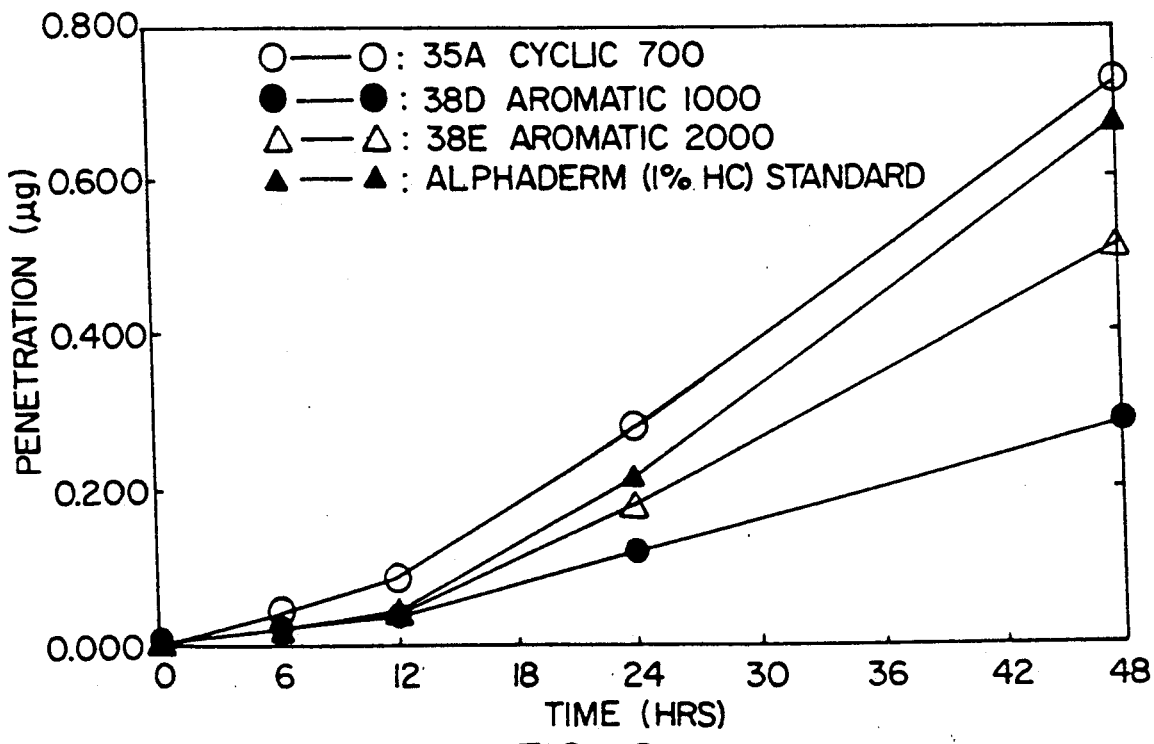
FIG._2.

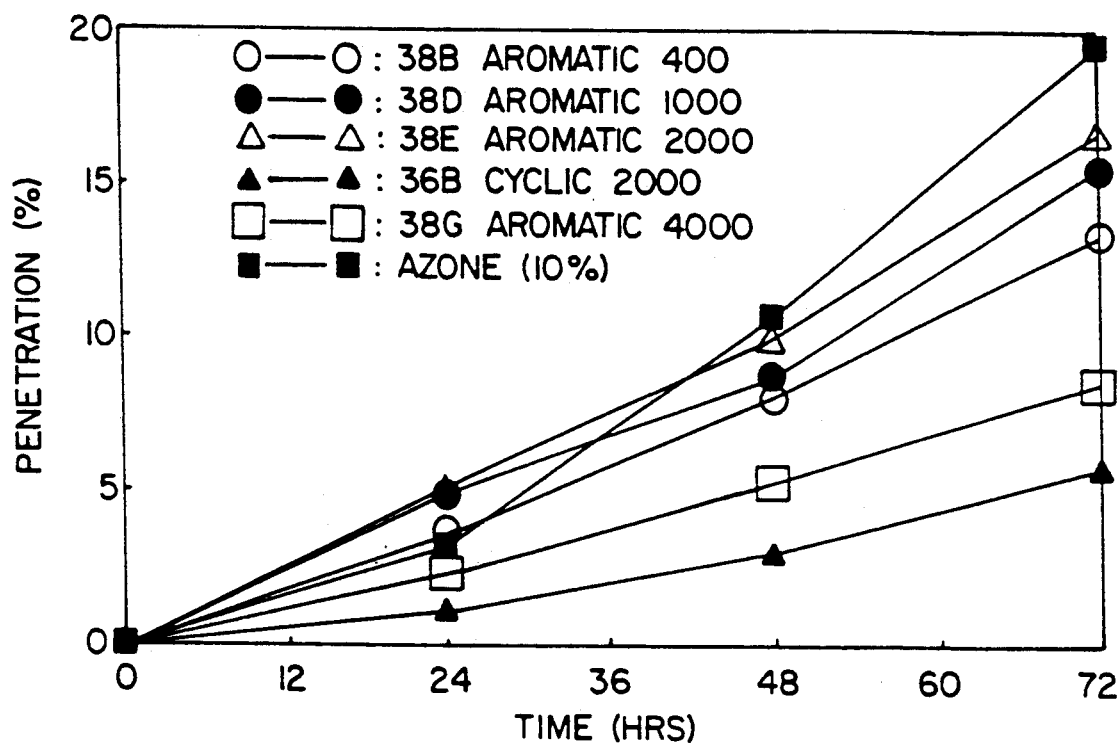
FIG._3.

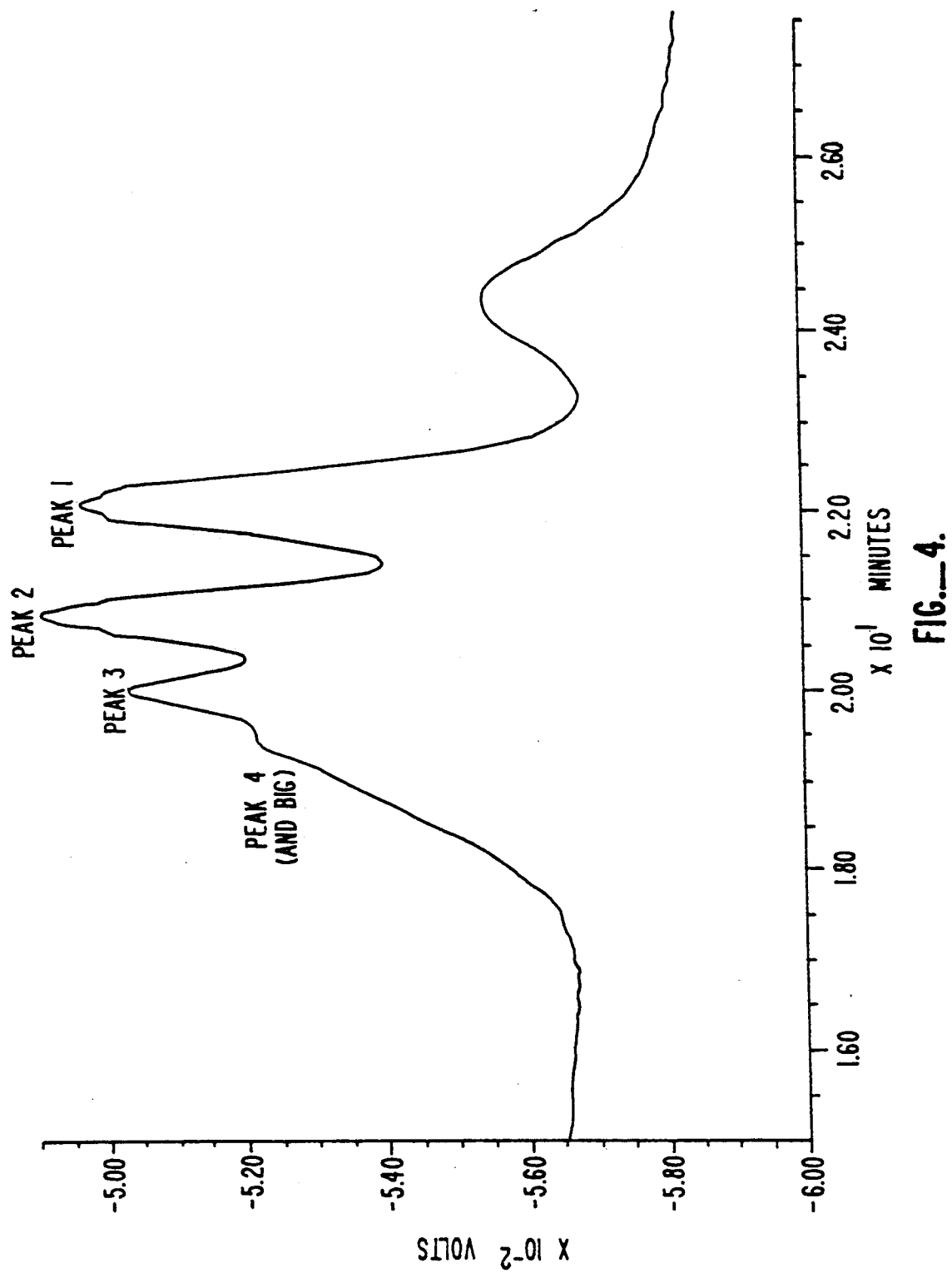
FIG._4.

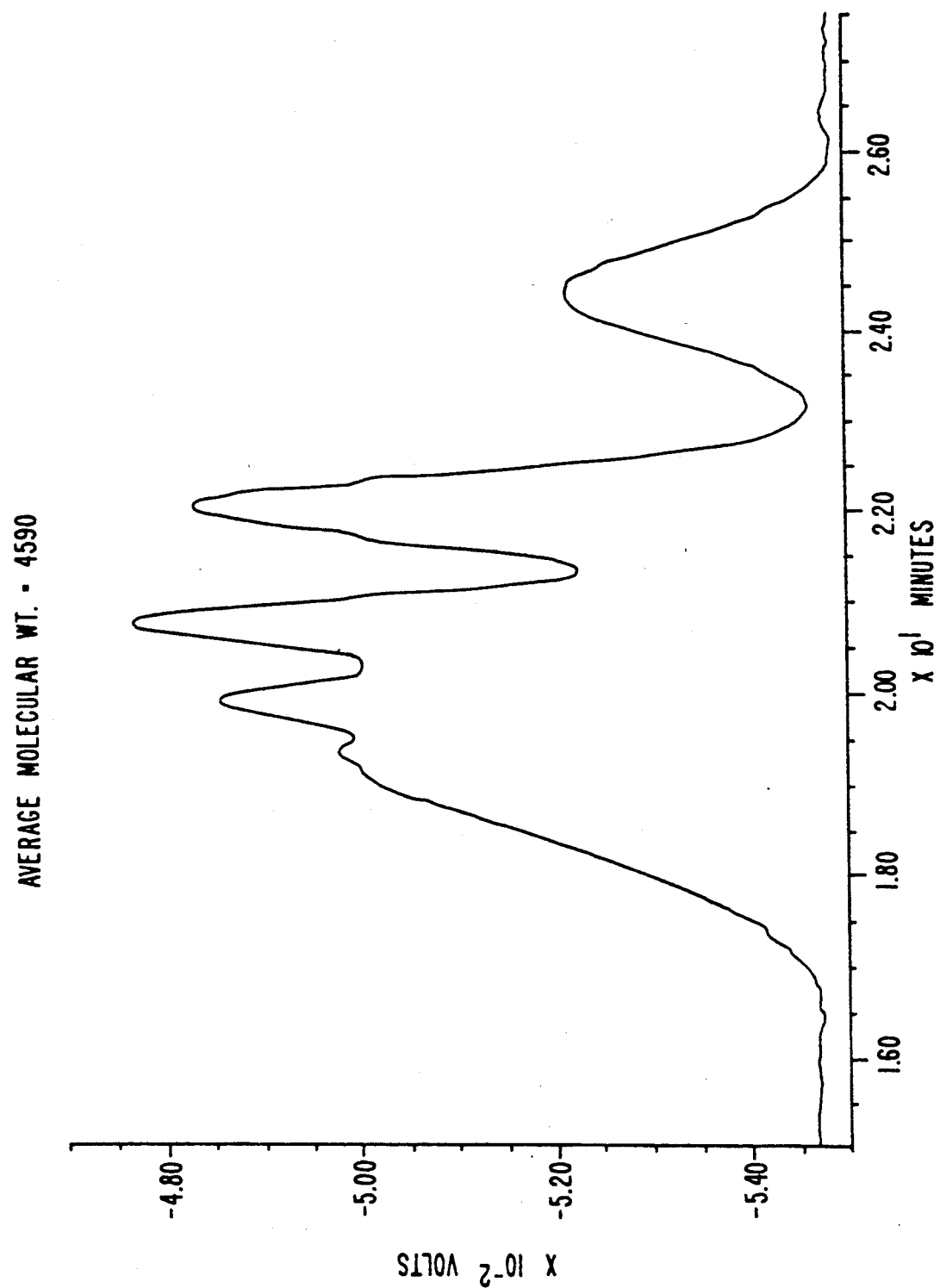

METHOD AND COMPOSITION FOR ENHANCING THE CUTANEOUS PENETRATION OF PHARMACOLOGICALLY ACTIVE AGENTS

This is a division of application Ser. No. 408,757, filed Sept. 18, 1989, now U.S. Pat. No. 4,971,800; which is a continuation-in-part of U.S. patent application Ser. No. 216,804, filed July 8, 1988, now abandoned, which in turn was a continuation-in-part of U.S. patent application Ser. No. 074,262, filed July 16, 1987, now abandoned.

FIELD OF THE INVENTION

This invention relates generally to topical or transdermal administration of pharmacologically active agents and more particularly relates to methods and compositions for enhancing the permeability of the skin to achieve enhanced cutaneous penetration of such agents.

BACKGROUND OF THE INVENTION

The delivery of drugs through skin provides many advantages; primarily, such a means of delivery is a comfortable, convenient and non-invasive way of administering drugs. The variable rates of absorption and metabolism encountered in oral treatment are avoided, and other inherent inconveniences—e.g., gastrointestinal irritation and the like—are eliminated as well. Transdermal drug delivery also makes possible a high degree of control over blood concentrations of any particular drug.

Skin is a structurally complex, relatively thick membrane. Molecules moving from the environment into and through intact skin must first penetrate the stratum corneum and any material on its surface. They must then penetrate the viable epidermis, the papillary dermis, and the capillary walls into the bloodstream or lymph channels. To be so absorbed, molecules must overcome a different resistance to penetration in each type of tissue. Transport across the skin membrane is thus a complex phenomenon. However, it is the cells of the stratum corneum which present the primary barrier to absorption of topical compositions or transdermally administered drugs. The stratum corneum is a thin layer of dense, highly keratinized cells approximately 10-15 microns thick. It is believed to be the high degree of keratinization of these cells which creates in most cases a substantially impermeable barrier to drug penetration.

In order to increase skin permeability, and in particular to increase the permeability of the stratum corneum, the skin may be pretreated with one or more penetration-enhancing agents prior to application of a medicament. Alternatively, and preferably, a drug and potentiator are concurrently delivered.

Various compounds for enhancing the permeability of skin are known in the art. U.S. Pat. Nos. 4,006,218, 3,551,554 and 3,472,931, for example, respectively describe the use of dimethylsulfoxide (DMSO), dimethyl formamide (DMF) and N,N-dimethylacetamide (DMA) to enhance the absorption of topically applied drugs through the stratum corneum. Other compounds which have been used to enhance skin permeability include decylmethylsulfoxide ($C_{10}$MSO), polyethylene glycol monolaurate (PEGML; see, e.g., U.S. Pat. No. 4,568,343), and the 1-substituted azacycloheptan-2-ones, particularly 1-n-dodecylcyclazacycloheptan-2-one (available under the trademark "Azone" from Nelson Research & Development Co., Irvine, Calif.; see U.S. Pat. Nos. 3,989,816, 4,316,893 and 4,405,616). The compounds of the prior art, however, suffer from one or more disadvantages. Clinical use has been limited by either the penetration of the agent itself, a problem widely noted with DMSO, or by cutaneous irritation, encountered, inter alia, with $C_{10}$MSO and the 1-substituted azacycloheptan-2-ones.

In selecting a penetration-enhancing potentiator, or "permeation enhancer," it is essential that adverse systemic effects and irreversible damage to the skin structure be avoided. It is also desirable that the compound itself not cause irritation or allergic response.

SUMMARY OF THE INVENTION

Accordingly, it is an object of the present invention to overcome the aforementioned disadvantages of the prior art.

It is another object of the invention to provide a composition for topical or transdermal administration of a pharmacologically active agent which increases the permeability of skin and mucosa and thus allows for enhanced cutaneous or mucosal penetration of the agent. In addition to a selected pharmacologically active agent, the composition contains one or more urethane compounds as a permeation enhancer, preferably dispersed within a topical carrier, and a selected pharmacologically active agent.

It is still another object of the invention to provide a method of increasing the permeability of the skin and thus enhancing the cutaneous penetration of a pharmacologically active agent, the method comprising applying the agent to skin or other epithelial tissue in conjunction with one or more urethane compounds that serves as a permeation enhancer.

It is a further object of the invention to facilitate the adherence of locally administered topical compositions containing cosmetics, sunscreens, insect repellents, or the like via co-administration with enhancers as will be described.

It is still a further object of the invention to provide a method of moisturizing or softening skin comprising contacting the skin surface with a composition containing a urethane compound as defined herein.

Additional objects, advantages and novel features of the invention will be set forth in part in the description which follows, and in part will become apparent to those skilled in the art on examination of the following, or may be learned by practice of the invention.

It has now been discovered that hydroxy-terminated urethane compounds prepared by reacting two moles of a hydroxy-terminated linear alkylene or polyalkylene glycol or polyether with one mole of a monomeric organic diisocyanate are excellent permeation enhancers which potentiate or facilitate the skin's permeability to pharmacologically active agents with which these discrete urethane compounds are formulated.

These hydroxy-terminated urethane compounds are represented by the general formula:

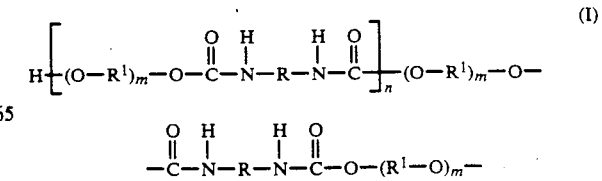

-continued

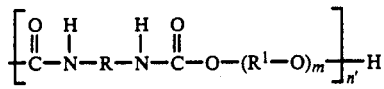

wherein R represents an alkylene or alkenylene radical, generally one containing from about one to about 20 carbon atoms, such as methylene, trimethylene and dimethyltrimethylene radicals, and in the case of the alkenylene radicals, one having between one and about 3 double bonds, or a cycloalkylene or cycloalkenylene radical, generally one containing from about 5 to about 10 carbon atoms, such as cyclopentylene, cyclohexylene and cyclohexenylene radicals, or a mononuclear or fused ring arylene radical, generally one containing from about 6 to about 10 carbon atoms, such as phenylene or naphthylene, all of which can be unsubstituted or substituted, e.g., with alkyl groups, generally ones containing up to about 6 carbon atoms, aryl groups which may be substituted with amine moieties, nitro, lower (1-6 C) alkyl, lower (1-6 C) alkoxy, lower (1-6 C) alkoxy-substituted lower (1-6 C) alkyl, halogen, and the like. $R^1$ represents the same or different alkylene or alkenylene radicals, generally ones containing from about 2 to 6 carbon atoms, such as $-CH_2CH_2-$ and $-CH_2CH_2CH_2-$, and in the case of the alkenylene radicals, ones typically having one or two double bonds; m is an integer selected so as to provide an $-(O-R')-$ moity having a molecular weight of from about 40 to about 6,000, more typically from about 400 to about 2,000, and n and n' are the same or a different integer of from 0 to 30, inclusive, correlated with m so as to provide a penetration enhancer having a molecular weight of up to about 200,000, more typically from about 220 to about 37,000, and preferably from about 1,000 to about 15,000.

In one embodiment, the present invention is directed to an adherent composition that facilitates the adherence of an agent applied to hair or skin.

In a second embodiment, the present invention is directed to a penetration-enhancing composition for topical application which allows for enhanced cutaneous or mucosal penetration of a pharmacologically active agent, the composition including a permeation enhancer in combination with an effective amount of a pharmacologically active agent. The potentiator compound is one or more of the aforementioned urethane compounds, and is preferably dispersed within a suitable topical carrier.

In another embodiment, the invention is directed to a method for administering a drug using the novel compositions, comprising contacting skin or other epithelial tissue, e.g., mucosal tissue, with a composition containing one or more of the aforementioned urethane compounds as a permeation enhancer and a selected pharmacologically active agent.

In still another embodiment, the invention is a method for moisturizing or softening the skin, comprising applying to skin surface a composition containing one or more of the aforementioned urethane compounds as will be described.

BRIEF DESCRIPTION OF THE DRAWINGS

FIG. 1 graphically illustrates a comparison of penetration enhancement provided by methotrexate compositions prepared according to the invention with that provided by an optimized standard;

FIG. 2 graphically illustrates a comparison of penetration enhancement provided by enhancer compositions prepared according to the invention with that provided by a known composition; and FIG. 3 graphically illustrates a comparison of penetration enhancement provided by urea compositions prepared according to the invention with that provided by urea compositions formulated with a known enhancer.

FIGS. 4 and 5 are chromatograms obtained by gel permeation chromatography carried out as described below on 35A Cyclic 700 and the compound of Example 5 below, respectively, to determine the molecular weights of these substances.

DETAILED DESCRIPTION OF THE INVENTION

The invention relates primarily to compositions for facilitating the adherence of an agent applied to hair or skin, and for topical or transdermal administration of a pharmacologically active agent, which compositions increase the permeability of the skin or other epithelial tissue and thus allow for enhanced cutaneous penetration. The compositions of the invention include one or more of the aforementioned urethane compounds as an adherence facilitator or a permeation enhancer, preferably dispersed within a suitable topical carrier, and a selected agent, including pharmacologically active agents. The invention also comprises methods of enhancing adherence or penetration of agents, including pharmacologically active agents, using the novel compositions, as well as a method of moisturizing skin using selected urethane compounds.

"Penetration enhancement" or "permeation enhancement" as used herein relates to increasing the permeability of skin to one or more pharmacologically active agents so as to allow for cutaneous delivery of a pharmacologically active agent. The enhanced penetration effected through the use of the inventive compositions can be observed, for example, by measuring the rate of diffusion of pharmacologically active agent into or through animal or human skin using a diffusion cell apparatus.

By "cutaneous" or "dermal" delivery, applicants intend to include both transdermal (or "percutaneous") administration, i.e. delivery by actual passage of a pharmacologically active agent through the skin (or other epithelial tissue such as buccal mucosa) into the blood stream, and local administration of a topical pharmacologically active agent as in, for example, the treatment of various skin disorders.

"Topical carriers" as used herein refer to carrier materials suitable for topical applications of drugs or cosmetics, and include any such materials known in the cosmetic and medical arts, e.g., any liquid or nonliquid carrier, gel, cream, ointment, lotion, emulsifier, solvent, liquid diluent, or the like, which does not adversely affect living animal tissue or interact with other components of the composition in a deleterious manner. Topical carriers are used to provide the compositions of the invention in their preferred liquid form. Examples of suitable topical carriers for use herein include water, liquid alcohols, liquid glycols, liquid polyalkylene glycols, liquid esters, liquid amides, liquid protein hydrolysates, liquid alkylated protein hydrolysates, liquid lanolin and lanolin derivatives, and like materials.

By the term "pharmacologically active agent" or "drug" as used herein is meant any chemical material or compound suitable for topical or transdermal administration which induces any desired local or systemic effect. Such substances include, the broad classes of compounds normally delivered through body surfaces and membranes, including skin. In general, this includes therapeutic agents in all of the major therapeutic areas including, but not limited to, anti-infectives such as antibiotics and antiviral agents, analgesics and analgesic combinations, anorexics, anthemidines, antiarthritics, antiasthmatic agents, anticonvulsants, antidepressants, antidiabetic agents, antidiarrheals, antihistamines, anti-inflammatory agents, antimigraine preparations, antimotion sickness, antinauseants, antineoplastics, antiparkinsonism drugs, antipruritics, antipsychotics, antipyretics, antispasmodics, including gastrointestinal and urinary, anticholinergics, sympathomimetics, xanthine derivatives, cardiovascular preparations including calcium channel blockers, beta-blockers, antiarrhythmics, antihypertensives, diuretics, vasodilators including general coronary, peripheral and cerebral, central nervous system stimulants, cough and cold preparations, decongestants, diagnostics, hormones, hypnotics, immunosuppressives, muscle relaxants, parasympatholytics, parasympathomimetics, psychostimulants, sedatives and tranquilizers.

Locally administered topical medicaments also fall within this category and include, for example, antibiotics, antifungals, antimicrobials, cutaneous growth enhancers including for the hair and nails, other hair care agents, including colorants and mascaras, pigment modulators, antiproliferatives, antipsoriatics, retinoids, anti-acne medicaments, antineoplastic agents, phototherapeutic agents, sunscreens, cutaneous protection agents, alpha-hydroxy acids including lactic and glycolic acids, and the like.

By "effective" amount of a pharmacologically active agent is meant a nontoxic but sufficient amount of a compound to provide the desired local or systemic effect and performance at a reasonable benefit/risk ratio attending any medical treatment. An "effective" amount of a permeation enhancer as used herein means an amount selected so as to provide the desired increase in skin permeability and, correspondingly, the desired depth of penetration, the rate of administration, and the amount of drug delivered.

The hydroxy-terminated linear alkylene or polyalkylene glycols or polyethers reacted with monomeric organic diisocyanates to form the nonpolymeric hydroxy-terminated urethane penetration enhancers of this invention are represented by the general formula:

H—(O—R¹)$_m$—H     (II)

wherein R¹ and m are as defined hereinabove for formula I. Included among these alkylene or polyalkylene glycols or polyethers are ethylene glycol, propylene glycol, butylene glycol and the like; polyalkylene ether glycols, such as polyethylene glycols, polypropylene glycols, polybutylene glycols, polytetramethylene glycols, polyhexamethylene glycols, polypropenylene glycols, and the like, which are obtained, for example, by acid-catalyzed condensation of lower alkylene oxides, such as ethylene oxide, propylene oxide, and the like, either with themselves or with glycols such as ethylene glycol, propylene glycol, propenylene glycol, and the like.

Polyalkylenearylene ether glycols which also have molecular weights ranging from about 40 to about 6000, more typically from about 400 to about 2,000, but which differ from the above-described polyalkylene glycols in having cycloalkylene or cycloalkenylene radicals, generally ones which contain from about 5 to about 10 carbon atoms, such as cyclopentylene, cyclohexylene, and cyclohexenylene radicals, or mononuclear or fused ring arylene radicals, all of which may either be unsubstituted or substituted, e.g., with alkyl groups, generally ones containing up to about 6 carbon atoms, amines, nitro, lower alkoxy, lower alkoxy-substituted lower (1–6 C) alkyl, halogen and the like, in place of some of the alkylene or alkenylene radicals of said polyalkylene glycols, may also be employed as polyalkylene glycol or polyether reactants.

Specific polyalkylene glycol or polyether reactants coming within the scope of formula II hereinabove include:
diethylene glycol,
triethylene glycol,
polyethylene glycol 300,
polyethylene glycol 400,
polyethylene glycol 600,
polyethylene glycol 900,
polyethylene glycol 1000,
polyethylene glycol 2000,
polypropylene glycol 400,
polypropylene glycol 700,
polypropylene glycol 1000,
polypropylene glycol 1200,
polypropylene glycol 2000,
polypropylene glycol 3000,
polypropylene glycol 4000,
polypropylene glycol 6000,
polytetramethylene glycols having molecular weights ranging from about 600 to 6000, and the like.

As can readily be appreciated, mixtures of the various reactive organic polyalkylene glycols or polyethers described hereinabove may also be employed in preparing the urethane penetration-enhancers used in the practice of the present invention.

A wide variety of monomeric organic diisocyanates represented by the general formula:

O=C=N—R—N=C=O     (III)

wherein R is as defined hereinabove for formula I, can be used to form the nonpolymeric hydroxy- or alkoxy-terminated urethane penetration enhancers of this invention. Included among such diisocyanates are aromatic diisocyanates, such as m-phenylenediisocyanate, p-phenylenediisocyanate, 4-t-butyl-m-phenylenediisocyanate, 4-methoxy-m-phenylenediisocyanate, 4-phenoxy-m-phenylenediisocyanate, 4-chloro-m-phenylenediisocyanate, toluenediisocyanates (either as a mixture of isomers, e.g., the commercially available mixture of 80% 2,4-toluenediisocyanate and 20% 2,6-toluenediisocyanate, or as the individual isomers themselves), m-xylylenediisocyanate, p-xylylenediisocyanate, cumene-2,4-diisocyanate, durenediisocyanate, 1,4-naphthylenediisocyanate, 1,5-naphthylenediisocyanate, 1,8-naphthylenediisocyanate, 2,6-naphthylenediisocyanate, 1,5-tetrahydronaphthylenediisocyanate, p,p'-diphenyldiisocyanate, diphenylmethane-4,4'-diisocyanate, 2,4-diphenylhexane-1,6-diisocyanate, "bitolylenediisocyanate" (3,3'-dimethyl-4,4'-biphenylenediisocyanate), "dianisidinediisocyanate" (3,3'-dimethoxy-4,4'-biphenylenediisocyanate); aliphatic diisocyanates, such as methylenediisocyanates, ethylenediisocyanate, the tri-, tetra-, penta-, hexa-, octa-, nona- and decamethylene-Ω,-Ω-diisocyanates, 2-chloro-trimethylenediisocyanate, 2,3-dimethyltetramethylenediisocyante, and the like, as well as mixtures thereof.

The urethanes of formula I above may be used to pretreat skin or other epithelial tissue prior to topical or transdermal administration of a pharmacologically active agent. Alternatively, and preferably, the penetration-enhancing urethane is administered concurrently with the pharmacologically active agent. The potentiator compound and drug may be administered with or without a topical carrier, although such a carrier is preferred. Where the composition includes a topical carrier, a formulation comprises from about 3-90 wt.% urethane compound, usually from about 5-25 wt.% urethane compound, and typically up to about 75 wt.%, carrier. Exemplary carriers herein include water, alcohols, including both monohydric and polyhydric alcohols, e.g. ethanol, isopropanol, glycerol, sorbitol, 2-methoxyethanol, diethylene glycol, ethylene glycol, hexylene glycol, mannitol and propylene glycol; ethers such as diethyl or dipropyl ether; polyethylene glycols and methoxypolyoxyethylenes; carbowaxes having molecular weights ranging from 200 to 20,000; polyoxyethylene glycerols; polyoxyethylene; sorbitols; and stearoyl diacetin. The topical carrier preferably includes both alcohol and water so as to accommodate lipophilic and hydrophilic drugs. An example of a particularly preferred formulation is a composition containing 25 wt.% urethane compound and 75 wt.% topical carrier, the carrier comprising 60 wt.% isopropanol or ethanol and 40 wt.% water.

The topical carriers described herein include various agents and ingredients commonly employed in dermatological and cosmetic ointments and lotions. For example, excipients, fragrances, opacifiers, preservatives, anti-oxidants, gelling agents, perfumes, thickening agents such as carboxymethylcellulose, stabilizers, surfactants, emollients, coloring agents and the like may be present.

It should be appreciated that the composition of the carrier can be varied to complement of the structure of the drug by making it more hydrophilic, e.g. by addition of water, or by making it more lipophilic, e.g. by addition of a long-chain alcohol.

The amount of pharmacologically active agent similarly will depend on a variety of factors, including the disease to be treated, the nature and activity of the agent, the desired effect (systemic or local or both), possible adverse reactions, the ability and speed of the agent selected to reach its intended target, the cost and availability of the agent, the use of two or more pharmacologically active agents, and other factors within the particular knowledge of the patient and physicians.

As noted above, the compositions of the present invention may be used with any number of pharmacologically active agents which may be topically or transdermally administered. Examples of exemplary pharmacologically active agents suitable for use in conjunction with the present invention include urea, vasodilators such as minoxidil, and lactic acid, e.g. in treating X-linked ichthyosis, a genetic skin disease characterized by excessive scaling.

The compositions of the present invention are similarly useful in facilitating the adherence of locally administered topical medicaments such as cosmetics, sunscreens, insect repellents or the like, and as skin emollients and moisturizing agents.

Any particular formulation will further depend on the chemical nature of the pharmacologically active agent to be administered as well as on the depth of cutaneous penetration desired. The method of delivery may also vary, but necessarily involves applying the formulation of the present invention to skin or other epithelial tissue for a period of time sufficient to allow the desired penetration of the selected drug or topical medicament. The method may involve direct application of the inventive composition as an ointment, gel, cream, or the like, or may involve use of a drug delivery device as taught, for example, in U.S. Pat. Nos. 3,742,951, 3,797,494 or 4,568,343.

Preferred drug delivery devices include a drug/permeation enhancer reservoir in the form of a matrix comprising rubber or other polymeric material, e.g. natural and synthetic rubbers such as polybutylene, polyisobutylene, polybutadiene, polyethylene, styrenebutadiene copolymers, polyisoprene, polyurethane, ethylene/propylene copolymers, polyalkylacrylate polymers, copolyesters, ethylene/acrylic copolymers, silicones and butadiene/acrylonitrile copolymers, ethylene/vinylacetate, gelled or thickened mineral oil, petroleum jelly and various aqueous gels and hydrophilic polymers. The matrix is applied to skin using a suitable adhesive as described, for example, in U.S. Pat. No. 4,568,343, supra.

The urethane compounds of formula I have also been discovered, surprisingly, to be useful as skin moisturizing agents. The invention thus includes a method of moisturizing skin using these compounds, and in particular includes a method of treating proliferative skin diseases. These conditions are typically characterized by epidermal cell proliferation or incomplete cell differentiation, and include, for example, X-linked ichthyosis, psoriasis, atopic dermatitis, allergic contact dermatitis, epidermolytic hyperkeratosis, and seborrheic dermatitis. Also included are ailments such as mange that are specific to nonhuman animals. A preferred formulation for use as a moisturizing agent is about 25 wt.% urethane in a topical carrier as described above. Such a formulation causes a urethane "barrier" to form at the skin surface, causing retention of moisture thereon.

Methods of synthesizing urethanes have long been known in the art. U.S. Pat. No. 2,266,777, for example, issued in 1941, describes the reaction of isocyanate compounds with polyhydroxy alcohols to give polyurethanes, now a standard synthetic method. Reference may also be had to Saunders, *Polyurethanes: Chemistry and Technology* (New York: Wiley & Sons, 1961) for an overview of the chemistry of urethanes.

In preparing the urethane compounds of formula I, the mole ratio of diol to diisocyanate is about 2:1, and the reaction is carried out at elevated temperature (at least about 100° F. and preferably at least about 150° F.; temperatures may be higher depending on the particular reactants and on the amount of catalyst used) with constant mixing. The solvent used is a suitable hydrocarbon solvent such as dioxane, xylene, cyclohexane or the like. The use of catalysts is optional. Suitable catalysts include organic tin alkyl titanates or octoates and amines such as those in the Dabco group (i.e., Dabco DC-1, DC-2, R-8020, R-595, 33 LV, DF and WT, all available from Air Products and Chemicals, Inc., Allentown, Pa., under the "Dabco" trademark) and N-ethyl morpholine. Further information regarding analogous reactions may be found in U.S. Pat. Nos. 2,266,777 and 2,282,827, the disclosures of which are hereby incorporated by reference in their entirety.

The values of n and n' for the compounds of Formula I may be controlled during synthesis by varying the reaction temperature, the amount, if any, of water in the reaction mixture, and the starting materials. For example, a higher temperature will typically result in a more highly polymerized structure, i.e., one having a higher m value, while increasing the amount of water present will ordinarily give different molecular weight compounds. Selection of reaction conditions herein is believed to be well within the skill of the art, and may in any case be readily derived from the aforementioned references on urethane chemistry.

In order that those skilled in the art can more fully understand this invention the following examples are set forth. These examples are given solely for purposes of illustration, and should not be considered as expressing limitations unless so set forth in the appended claims. All parts and percentages are by weight unless otherwise stated.

EXAMPLE 1

Forty grams of polyethylene glycol 400 were admixed with 2–3 drops of stannous octoate in a 100 ml beaker, using a Teflon stirring bar, for 5 minutes. Then, 8.7 grams of toluene diisocyanate were slowly added, with stirring, in small increments, taking care not to let the reaction temperature exceed about 160° F. Once all the toluene diisocyanate had been added, the reaction mixture was stirred for an additional 40 minutes while the temperature was maintained at about 160° F., then allowed to cool to room temperature. The resulting urethane compound can be represented by the formula:

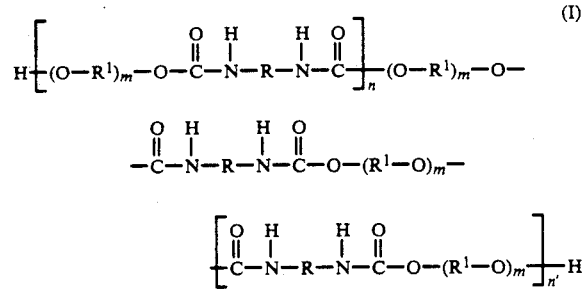

wherein m is a number such that the number of oxyethylene groups in each polyethylene glycol moiety give that moiety an average molecular weight of about 400. In this example, as well as in the examples which follow, completion of the reaction and identification of the product were confirmed by infrared spectroscopy. Unless otherwise noted, all reagents used in these examples were obtained from either Union Carbide Corporation (New York, N.Y.) or Dow Chemical (Midland, Mich.).

EXAMPLE 2

Forty grams of polyethylene glycol 400 were admixed with 0.08 grams of stannous octoate in a 100 ml beaker, using a Teflon stirring bar, for 5 minutes. Then, 13.1 grams of dicyclohexylmethane diisocyanate were slowly added, with stirring. After all of the dicyclohexylmethane diisocyanate was added, the mixture was stirred for an additional 30 minutes. Then, an additional 1 cc of stannous octoate was added, and the mixture was stirred for an additional 10 minutes. At this time, an exothermic effect was noted. The mixture was allowed to react at 160° F. for 2 hours, then cooled to room temperature.

EXAMPLES 3–11

A series of urethane compounds were prepared using different polypropylene glycols listed in Table I and dicyclohexylmethane diisocyanate. The procedure of Example 1 was followed, using two moles of polypropylene glycol to each mole of dicyclohexylmethane diisocyanate, except that the reaction mixture was maintained at a temperature between 150° F. and 160° F. while being stirred for an additional 30 minutes.

TABLE I

| Example | Polypropylene Glycol |
| --- | --- |
| 3 | Dipropylene Glycol |
| 4 | Polypropylene Glycol 410 |
| 5 | Polypropylene Glycol 725 |
| 6 | Polypropylene Glycol 1000 |
| 7 | Polypropylene Glycol 1200 |
| 8 | Polypropylene Glycol 2000 |
| 9 | Polypropylene Glycol 2000 |
| 10 | Polypropylene Glycol 3000 |
| 11 | Polypropylene Glycol 4010 |

EXAMPLES 12–18

The procedure of Example 1 was followed to prepare a series of urethane compounds using the different polypropylene glycols listed in Table II and toluene diisocyanate, in the ratio of two moles of polypropylene glycol to one mole of toluene diisocyanate.

TABLE II

| Example | Polypropylene Glycol |
| --- | --- |
| 12 | Dipropylene Glycol |
| 13 | Polypropylene Glycol 400 |
| 14 | Polypropylene Glycol 725 |
| 15 | Polypropylene Glycol 1000 |
| 16 | Polypropylene Glycol 2000 |
| 17 | Polypropylene Glycol 3000 |
| 18 | Polypropylene Glycol 4000 |
| 10 | Polypropylene Glycol 3000 |
| 11 | Polypropylene Glycol 4010 |

EXAMPLES 19–21

A series of urethane compounds were prepared using different polypropylene glycols, listed in Table III, and methylene bis(4-phenylisocyanate). The procedures and conditions of Example 1 were followed with the exception that the reaction mixture was heated to, and maintained at, a temperature between 160° F. and 170° F. while being stirred for an additional hour.

TABLE III

| Example | Polypropylene Glycol |
| --- | --- |
| 19 | Polypropylene Glycol 1000 |
| 20 | Polypropylene Glycol 1200 |
| 21 | Polypropylene Glycol 2000 |

EXAMPLE 22

Using the procedure and reaction conditions of Example 1, 72.5 grams of melted polyethylene glycol 1450 were admixed with 26.2 grams of dicyclohexylmethane diisocyanate and two drops of stannous octoate.

EXAMPLE 23

The procedure of Example 3 was repeated replacing the dipropylene glycol with 45 grams of polyethylene glycol 900.

EXAMPLE 24

Twenty grams of polypropylene glycol, m.w. approximately 2000 (manufactured by Olin Chemical Co., Stamford, Conn., under the trademark "Poly G-55-56") were admixed with 1.25 grams of methylene bis(4-phenylisocyanate) and two drops of stannous octoate using the reaction conditions and procedure of Example 19.

EXAMPLE 25

The procedure of Example 24 was repeated using 30 grams of polyethylene glycol 600, 6.55 grams of dicyclohexylmethane diisocyanate and two drops of stannous octoate.

EXAMPLE 26

The procedure of Example 25 was repeated using 30 grams of polyethylene glycol 600, 6.35 grams of 4,4-diphenylmethane diisocyanate, and three drops of stannous octoate.

EXAMPLE 27-29

The procedure of Example 19 was repeated using two moles of the different polypropylene glycols shown in Table IV and one mole of 4,4'-diphenylmethane diisocyanate.

TABLE IV

| Example | Polypropylene Glycol |
| --- | --- |
| 27 | Polypropylene Glycol 3000 |
| 28 | Polypropylene Glycol 4000 |
| 29 | Mixture of Polypropylene Glycol 1025 and 425-average mw = 700 |

EXAMPLE 30

The procedure of Example 19 was repeated using 50 grams of polypropylene glycol 1025, four grams p-phenylene diisocyanate and three drops of stannous octoate, except the mixture was stirred for one hour at 140° F. to 150° F.

EXAMPLE 31

Thirty-six grams of melted polyethylene glycol 900 at 90° F. were admixed with 1.74 grams of toluene diisocyanate, using the reaction conditions and procedure of Example XXX. The resulting urethane compound can be represented by the formula:

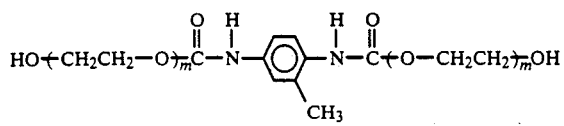

wherein m is a number such that the number of oxyethylene groups in each polyethylene glycol moiety give that moiety an average molecular weight of about 900.

EXAMPLE 32

Fifty grams of polypropylene glycol 1000 were admixed with 33.5 grams of polyethylene glycol 3350, 7.8 grams of dicyclohexylmethane diisocyanate and three drops of stannous octoate using the reaction conditions and procedures of Example 19.

EXAMPLE 33

In Vitro Percutaneous Penetration Studies

The urethane compounds of the preceding examples were used as vehicles for selected drugs (urea, hydrocortisone, methotrexate). In vitro skin transport studies were done to determine the effect of the urethane-containing vehicles on drug penetration. These tests were conducted using standard Franz in vitro percutaneous diffusion cells with excised pig skin (as described in T. J. Franz, *J. Invest. Dermatol.* 64:190–195 (1975) and in T. J. Franz, "The Finite Dose Technique as a Valid In Vitro Model for the Study of Percutaneous Absorption in Man" in *Current Problems in Dermatology*, vol. 7, pages 58–68, Ed. J. W. H. Mali (Karger, Basel 1978)).

Excised pig skin was mounted between the cylindrical glass cell cap and the cell body, with the epidermal surface facing outward, and the dermal surface bathed from below with isotonic saline. The temperature of the chamber was maintained at 37° C. by water circulated through the jacketed cell chamber. A Teflon-covered magnet stirring bar, driven by an external magnet mounted on a timing motor, kept the saline solution in constant motion. Radiolabeled drug was added to the test formulation as a tracer, which was uniformly applied in small quantities (0.05–0.25 grams total formulation) to the epidermal surface of the skin. At sequential time intervals (e.g., 6 hr, 12 hr, 36 hr, 48 hr) 1 ml aliquots of saline from the dermal reservoir were removed through the sampling port provided for that purpose. The radio-activity (tritum) or carbon-14 ($^{14}$C) of the tracer compound which penetrated through the skin into the reservoir was determined by liquid scintillation counting. The total quantity of drug which penetrated for each time interval was then calculated based on the specific activity of the formulation which was applied to the skin's surface.

For these studies the urethane compounds were formulated into test vehicles by mixing 2.5 grams of urethane compound with 5.0 grams of isopropyl alcohol and 2.5 grams of distilled water. Tracer amounts of radiolabeled urea, hydrocortisone, or methotrexate were added to the vehicle, usually at a total drug concentration of 1%. The studies evaluated vehicles containing various urethane compounds, with diverse chemical structures and properties and varying molecular weights for their ability to facilitate drug transport across skin. FIGS. 1, 2 and 3 summarize the effects of selected urethane compounds in enhancing drug penetration through skin:

(a) FIG. 1 shows that all urethane compounds tested produced enhanced percutaneous penetration of 1% methotrexate versus an optimized standard 1% methotrexate formulation. The compounds tested in FIG. 1 were as follows: "35A Cyclic 700" was the reaction product of 2 moles polypropylene glycol, average m.w. approximately 700, with 1 mole of dicyclohexylmethane diisocyanate; "38D Aromatic 1000" was the reaction product of 2 moles polypropylene glycol, average m.w. approximately 1000, with 1 mole toluene diisocyanate; and "77E Biphenyl 700" was the reaction product of 2 moles of polypropylene glycol, m.w. approximately 700, with 1 mole.diphenylmethane-4,4'-diisocyanate.

(b) In FIG. 2, various aromatic urethane compounds with propylene glycol (PPG), average molecular weights ranging from 700 to 2000 were compared with an optimized formulation of 1% hydrocortisone (available under the trademark "Alphaderm" from Morton-Norwich Products, Norwich, N.Y.). (In FIG. 2, compound "38E Aromatic 2000" was the reaction product of 2 moles polypropylene glycol, average m.w. approximately 2000, with 1 mole of toluene diisocyanate.) The penetration of hydrocortisone in urethane compound 35A Cyclic 700 (see (a) above) was comparable to that of Alphaderm.

(c) In FIG. 3, the penetration of 1% urea in various aromatic and cyclic urethane compounds with PPG molecular weight ranging from 400 to 4000 was compared with an Azone-containing formulation. The compounds used were as follows: "35B Aromatic 400" was the reaction product of 2 moles of polypropylene glycol, m.w. approximately 400, with 1 mole of toluene diisocyanate; "36B Cyclic 2000" was the reaction product of 2 moles of polypropylene glycol, average m.w. approximately 2000, with 1 mole of dicyclohexylmethane diisocyanate; "38G Aromatic 4000" was the reaction product of 2 moles of polypropylene glycol, average m.w. approximately 4000, with 1 mole of toluene diisocyanate. Maximum urea penetration was achieved with the Azone formulation, followed closely by the aromatic urethane compounds (38D/38E), formulated with polypropylene glycol, m.w. 1000-2000. The lowest urea penetration was obtained with the Cyclic 2000 and Aromatic 4000 urethane compounds.

The molecular weights of the urethane compounds of this invention can be determined on a Waters Associates (Milford, Mass.) liquid chromatograph consisting of Model 510 pump, a U6K sample ejector and a Model 410 refractive index detector. Typically, the column set is one 1000A and two 500A Ultrastyragel gel permeation chromatography columns, each 7 mm inside diameter and 30 cm in length. Tetrahydrofuran, pumped at a flow rate of 1.0 ml/min, is the solvent. The system is microcomputer controlled using Maxima 820 software supplied by Dynamic Solutions (a division of Waters Associates).

Calibration of the column set is performed using polypropylene glycol standards (Scientific Polymer Products, Inc., Ontario, N.Y.) for molecular weights below 4,000 daltons, and polystyrene for molecular weights up to 200,000 daltons. All molecular weights are referenced to the calibration with these standards. Samples are prepared as 0.1% (1000 ppm) solutions in tetrahydrofuran, and 100 ul of the thus-prepared solutions are injected for each analysis.

With reference to FIG. 4, a typical chromatogram of 35A Cyclic 700, the composition of this material, based on uncorrected peak areas of the chromatogram, falls within the following ranges:

| Peak | Composition* |
|---|---|
| 1 | PPG—I—PPG 25-35% |
| 2 | PPG—I—PPG—I—PPG 18-30% |
| 3 | PPG—I—PPG—I—PPG—I—PPG 14-22% |
| 4 | larger oligomeric species 10-30% |

*PPG = polypropylene glycol, average molecular weight = approximately 700; I = dicyclohexylmethane diisocyanate.

IN VIVO PHARMACOLOGICAL EFFECTS OF TOPICAL DRUGS FORMULATED IN URETHANE COMPOUNDS

EXAMPLE 34

Topical application daily for 10 days of 1% methotrexate (MTX) in urethane compound 35A Cyclic 700 to the backs of hairless mice produced 47% inhibition of DNA synthesis in the treated skin, as assessed autoradiographically by epidermal labeling indices. The topically applied methotrexate was absorbed and produced similar degrees of inhibition of DNA synthesis in the untreated abdominal skin.

TABLE V

Effect of Topical 1% Methotrexate in Urethane Compound 35A on Epidermal DNA Synthesis in Hairless Mice

| Site | Treatment | Labeling Index | % Inhibition | (p value) |
|---|---|---|---|---|
| Back | 35A | 3.25 ± 1.71 | — | |
| | 1% MTX | 1.77 ± 1.66 | 47 | 0.078 |
| Abdomen | 35A | 3.57 ± 1.40 | — | |
| (untreated) | 1% MTX | 1.85 ± 2.19 | 48 | 0.100 |

35A (n = 8)
MTX (n = 7)
Treatments daily × 10
MTX (Sigma)

EXAMPLE 35

Topical application of 10% lactic acid in urethane compound 36C (PPG 1000) daily markedly decreased scaling in X-linked ichythosis after 7-10 days of treatment. This clinical effect was obtained in the absence of irritation or allergenicity.

EXAMPLE 36

The formulations listed in Table VI below were prepared for use in toxicity studies by mixing the indicated ingredients, in the indicated amounts, in a glass beaker in the following manner. The oil phase components (petrolatum, sorbitan mono-oleate, and urethane compound) were weighed out and liquified together at 70 degrees C. Methotrexate, if part of the composition, was dissolved in purified water to which was then added sodium hydroxide and propylene glycol at approximately 40 degrees C., using a magnetic stirrer for mixing. The pH was measured to confirm that the solution was in the range of 5.0 to 6.5.

TABLE VI

| Component | A; 1% Methotrexate Ointment; Parts[2] | B; Ointment Vehicle; Parts | C; 0.25% Methotrexate Ointment; Parts | D; 1% Methotrexate Ointment; Parts | E; Ointment Vehicle;[1] Parts |
|---|---|---|---|---|---|
| Methotrexate | 1.0 | — | 0.25 | 1.00 | — |
| White petroleum | 76.50 | 77.50 | 78.25 | 77.50 | 78.50 |
| Urethane compound[3] | 10.00 | 10.0 | 10.00 | 10.00 | 10.00 |
| Propylene glycol | 7.50 | 7.5 | 7.50 | 7.50 | 7.50 |
| Tween 20[4] | 1.0 | 1.0 | — | — | — |
| Sorbitan monooleate | 2.0 | 2.0 | 2.00 | 2.00 | 2.00 |

TABLE VI-continued

| Component | A; 1% Methotrexate Ointment; Parts[2] | B; Ointment Vehicle; Parts | C; 0.25% Methotrexate Ointment; Parts | D; 1% Methotrexate Ointment; Parts | E; Ointment Vehicle;[1] Parts |
|---|---|---|---|---|---|
| 10% Aqueous NaOH solution[5] | 0.12 | — | 0.31 | 1.24 | — |
| Purified Water | 1.88 | 2.0 | 1.69 | 0.76 | 2.00 |

[1] 0.25 Part FD&C Yellow #5 also added.
[2] All parts given are per 100 parts of formulation.
[3] A polypropylene glycol 725 dicyclohexylmethane diisocyanate urethane compound prepared as described in Example V hereinabove, average molecular weight 4500 as determined by gel permeation chromatography.
[4] Polyoxyethylene (20) sorbitan monolaurate.
[5] Added to adjust pH of aqueous phase to 5.0–6.5 prior to mixing with petrolatum.

The aqueous solution was then added to the hot oil phase under vigorous stirring conditions. This mixture was then cooled on the laboratory bench at room temperature until it was too viscous for proper stirring. The mixture was then mixed with a spatula by hand until it cooled to room temperature. Containers were then filled with the formulations.

EXAMPLE 37

Eye irritation studies in rabbits were conducted as follows. One hundred milligrams of formulation a (1% methotrexate ointment) were instilled into one eye of each of six albino rabbits, with no subsequent rinse. Gross observations were performed daily under white light and under longwave ultraviolet light subsequent to fluorescein staining. The ointment produced a 24-hour primary eye irritation score of 0.0, with no animals producing positive irritation responses. Thus, this formulation was classed as non-irritating.

The corresponding vehicle control ointment (formulation B) produced a 24-hour primary eye irritation score of 0.3, with no animals producing positive irritation responses per the laboratory scoring system. All evidence of irritation was resolved by day 2. Thus, this control formulation was classed as practically non-irritating.

EXAMPLE 38

Hypersensitivity studies in Hartley strain Guinea pigs were conducted as follows. A modified Maguire test design was utilized (Maguire, *J. Soc. Cosm. Chem.* 24:151-162 (1973)) in which Complete Freund's Adjuvant was employed to intensify a hypersensitivity response, if present. Four 0.5 ml doses of either formulation A (1% methotrexate ointment) or the corresponding vehicle control ointment (formulation B) were applied to six Guinea pigs whose shoulder areas of skin had been excoriated with sandpaper. Induction doses were performed on days 0, 2, 4 and 7.

On day 21 one topical dose of 0.5 g of test substance was applied as a 10% mixture in petrolatum. No allergic contact dermatitis was produced.

The highest non-irritating concentration of each test substance in water was 10%. At a concentration of 25%, one of six animals treated with formulation A exhibited a barely perceptible erythemal response at 24 hours, which was gone by 48 hours. Four of six animals treated with a concentration of 25% of formulation B exhibited a barely perceptible erythemal response, which persisted for 72 hours for two of the animals.

EXAMPLE 39

0.5 gram of either formulation A (1% methotrexate ointment) or the corresponding vehicle control ointment (formulation B) was applied to the clipped intact and abraded skin of each of 6 adult male and female albino rabbits over a 24-hour period, using a 1"×1 inch gauze patch taped to the animals' torsos with 1" wide non-irritating tape. Observations for erythema and edema were performed at 24 and 72 hours after application.

Each formulation produced a skin irritation score of 0.5. Since a score of 5 or more is required for a material to be classed as a primary irritant, neither formulation was considered to be a primary skin irritant. Minimal erythema of intact and abraded skin sites was observed at 24 hours for all animals. However, no erythema was observed for any of the test animals at 72 hours.

EXAMPLE 40

A study was conducted to evaluate the effectiveness and safety of methotrexate-containing topical formulations prepared as described in Example 36 hereinabove in the treatment of plaque psoriasis.

I. Patient Population

The study enrolled 26 patients, of whom 15 completed all ten weeks of the study and 11 dropped out before completion. Nineteen subjects completed at least 8 weeks of treatment. The 11 subjects who discontinued their participation in the study did so for the following reasons:

5 - subject disinterest
4 - General worsening of untreated psoriasis.
1 - lack of effectiveness of formulations tested
1 - Removal due to low white blood cell count.[1]
1. Inclusion criteria were:
   At least 18 years old.
   Males.
   Females who are postmenopausal, surgically sterile, or using a medically acceptable form of birth control with a negative serum pregnancy test.
   Diagnosis of plaque psoriasis.
   At least two comparable mile, moderate, or moderately severe symmetrical lesions, with each lesion approximately 25 square centimeters.
   Stable or slowly exacerbating condition.
   Written informed consent.
2. Exclusion criteria were:
   Any medical condition which would preclude study participation, including renal or hepatic disorders, severe anemia, active infectious disease, history of skin cancer, excessive alcohol consumption, or other medical contraindication to methotrexate or vehicle components.
   Significant abnormal baseline laboratory values.
   Guttate, pustular, or erythrodermic psoriasis.
   Acute flaring of psoriasis.

-continued

Subject has used active topical medication (such as corticosteroids) within two weeks before entry to study or systemic therapy within one month before enrollment. Emollients are acceptable up to and during study enrollment except on sites to be evaluated.
Known hypersensitivity to any of the ingredients of the test medications.
Pregnant or nursing females.
Previously studied under this protocol.
Treatment with an investigational drug within one month before study enrollment.
Any subject with lesions covering greater than 20% of body surface area.

[1] See item No. 2 in the "Safety" section hereinbelow.

II. Results:

1. Efficacy

In this twelve-week double-blind, vehicle-controlled, paired comparison study, two methotrexate ointment formulations were compared to a common vehicle in the treatment of limited areas of skin of patients with plaque psoriasis. The subjects treated no more than eight square inches of lesions twice daily for up to ten weeks. Study patients were evaluated weekly through Day 28 and biweekly through Day 84 for objective signs of erythema, scaling and elevation; and subjective signs of pain, burning and itching of the treatment sites. Laboratory values for hematology, blood chemistry, pregnancy for fertile females, and routine urinalysis were monitored during the twelve weeks.

As of Feb. 16, 1989, nineteen subjects had completed at least eight weeks of treatment. The lesions were graded for scaling, erythema, and elevation. The combined scores for these three parameters were compared to the initial scores and expressed as percentage improvement, as shown in Table VII:

TABLE VII

| Improvement of Lesions Percentage of Subjects with Good-to-Excellent Improvement | |
|---|---|
| Treatment | Good to Excellent |
| Untreated | 16% |
| Vehicle Control | 25% |
| 0.25% Methotrexate | 54% |
| 1.00% Methotrexate | 62% |

Thus, a high percentage of subjects exhibited good-to-excellent clearing of the lesions treated with the methotrexate formulations relative to untreated lesions or to lesions treated with the vehicle control formulation. The number of lesions with good clearing responses correlated with the concentration of methotrexate in the ointment formulations. Twenty-three percent of the lesions treated with 1.00% methotrexate formulation cleared totally. This contrasts with 8% of the lesions treated with the 0.25% methotrexate formulation. No lesions in the two control groups cleared totally.

2. Safety

A. The formulations were found to be mild to the skin. There were no indications of irritation to the skin and no other local adverse affects attributable to the test materials.

B. There were no systemic side effects attributable to the test materials.

II. Summary

The formulations containing methotrexate and a urethane compound as a delivery aid were effective in reducing the symptoms of psoriasis, without irritation or discomfort.

EXAMPLE 41

An in vitro percutaneous penetration study was conducted to compare, in a series of runs:

(1) a composition containing 1% methotrexate in a vehicle made up a 50%:50% ethanol:water mixture, and (2) the composition described in (1) above to which there had also been added 10% of 35A Cyclic 700. The foregoing percentages were based on the total weights of the respective compositions. The procedure used was that of Example 33 above. The results obtained are given in Table VIII below.

| Composition | Amount of Methotrexate Penetrated (ug/24 hours)* |
|---|---|
| (1) | 0.58 ± 0.24 |
| (2) | 2.07 ± 0.24 |

*The two values are different at greater than a 95% confidence level.

EXAMPLE 42

Percutaneous penetration studies were conducted comparing Ointment vehicle E (Table VI above) containing 1% methotrexate and varying amounts of 35A Cyclic 700. The foregoing percentages were based on the total weights of the respective compositions, and the procedure used was again that of Example 33 above. The results obtained are given in Table IX below.

TABLE IX

| | Amount of Methotrexate Penetrated (ug/24 hours)* | | |
|---|---|---|---|
| Composition | Run 1 | Run 2 | Run 3 |
| Ointment vehicle E (control) | — | 1.35 ± 0.37 | 2.09 ± 0.72 |
| Ointment vehicle E plus 10% 35A Cyclic 700 | 2.87 ± 0.77 | 1.57 ± 0.23 | — |
| Ointment vehicle E plus 20% 35A Cyclic 700 | — | 2.12 ± 0.52* | 3.61 ± 1.75 |
| Ointment vehicle E plus 25% 35A Cyclic 700 | 9.04 ± 2.26* | — | — |

*This value is different from the other value(s) in the run at greater than a 95% confidence level.

Subsequent experiments have indicated that on average the delivery of methotrexate is doubled when the concentration of 35A Cyclic 700 in petrolatum-based ointment is increased from 10% to 25%.

EXAMPLE 43

A commercially available vehicle, "Vehicle N" (Neutrogena Corp., Los Angeles, Calif.), containing ethanol, isopropanol, propylene glycol, Laureth-4 (surfactant) and purified water, was used with and without 3%A Cyclic 700 to apply 1% of methotrexate (based on the total weights of the respective compositions) to the skin of MiniPigs, the purpose being to evaluate these compositions' effect on inhibition of DNA synthesis. Twenty milligrams of each composition was applied to 3 square centimeters on the dorsal surface of the Mini-Pigs twice a day for a total of 14 days. At 7 and 14 days the vehicle-treated and the methotrexate-trexate treated sits were injected with $^3$H-deoxyuridine, a precursor of DNA. Methotrexate blocks the incorporation of deoxyuridine into DNA. The effect of methotrexate on DNA synthesis was determined using autoradiography to score histologically the number of epidermal cells incorporating $^3$H-deoxyuridine.

The results of these experiments are given in Table X below.

TABLE X

| | Percent Inhibition of DNA Synthesis by Methotrexate (MTX)* | |
|---|---|---|
| Test Material | Percent Inhibition 7 Days | Percent Inhibition 14 Days |
| Vehicle N plus 1% MTX | No inhibition** | 21 ± 3 |
| Vehicle N plus 1% MTX and 25% 35A Cyclic 700 | 43 ± 7 | 35 ± 1.4 |

*Percent inhibition was determined relative to Vehicle N alone (0% inhibition).
**The methotrexate formulation caused stimulation of DNA synthesis at this time point.

EXAMPLE 44

The ability of 35A Cyclic 700 to increase the residence time of tetracycline on human skin in vivo was evaluated. Approximately 5 milligrams of an 0.22% solution of tetracycline in ethanol (this is the concentration of tetracycline in the commercial product Topicycline), and 5 milligrams of the same solution to which there had also been added 10%, based on the total weight of the solution, of 35A Cyclic 700, were applied to the skin of a test subject's arms. After 30 minutes, the skin was washed three times with a soap solution and a fourth time with 50% ethanol in water. The amounts of tetracycline on the skin before washing, and remaining on the skin after each washing, were graded by an observer's subjective evaluation of tetracycline's fluorescence intensity on the skin under an ultraviolet lamp.

The results of this evaluation are given in Table XI below.

TABLE XI

| | Fluorescence Intensity* | |
|---|---|---|
| Number of Washes | No 35A Cyclic 700 | 10% 35A Cyclic 700 |
| 0 | 3 | 3 |
| 1 | <1 | 2.5 |
| 2 | 0 | 2 |
| 3 | 0 | 1 |
| 4 | 0 | 1 |

*Graded on a subjective scale in which 0 = no fluorescence, 3 = starting intensity of fluorescence.

An experiment was conducted to assess the extent to which 35A Cyclic 700 penetrates skin.

Full thickness human cadaver skin, trimmed to remove subcutaneous tissue and stored in a freezer from removal at autopsy until used in this experiment, was placed on standard Franz percutaneous diffusion cells, each approximately 2 cm$^2$.

A 45% w/w solution of 35A Cyclic 700 was spiked with $^{14}$C lactic acid to achieve a concentration of 2 microcuries of $^{14}$C per 0.225 grams of formulation. The radioactive tracer was used to insure that none of the diffusion cells were leaky, as determined by measurement of radioactivity in the reservoirs (data not presented). No leaky cells were found.

225 milligrams of the 35A Cyclic 700 solution was added to each diffusion cell. After 24 hours, the entire contents of each reservoir was collected and extracted into methylene chloride. The extracts were then pooled into four groups, as described in Table XII below.

TABLE XII

| Sample No. | Number of Cells Combined | Volume of Extract (ml) |
|---|---|---|
| 1 | 12 | 65 |
| 2 | 11 | 70 |
| 3 | 12 | 82 |
| 4 | 11 | 70 |

Next, each of the four methylene chloride extracts was evaporated to dryness, then reconstituted in one ml of tetrahydrofuran. One hundred fifty ul of each sample was then passed through a gel permeation chromatography column to determine if any material chromatographed in the region were 35A Cyclic 700 would be expected.

There was no detectable 35A Cyclic 700 in the extracts at the limit of detection of this substance (50 ug) in the system. Some high molecular weight material that absorbed in the UV portion of the spectrum (at 254 nm) was found in the extracts. This was probably material extracted from the skin during the penetration phase of the experiment, since 35A Cyclic 700 does not absorb at 254 nm.

It is possible that some 35A Cyclic 700 could be present, hidden by the UV absorbing material on the column, since some of this UV absorbing material chromatographs in the region where 35A Cyclic 700 would be expected. If this were so, however, there still would be less than 50 ug of 35A Cyclic 700 per combined sample, based upon comparison with standards.

If all of the 35A Cyclic 700 had penetrated the skin samples and had been recovered in this experiment, the final extracts from Samples Nos. 1 and 3 would each have contained 1215 mg/ml of this substance, while the final extracts from Samples Nos. 2 and 4 would each have contained 1114 mg/ml of 35A Cyclic 700. Since, as shown in Table XIII below, <50 ug of 35A Cyclic 700 was detected in 0.15 ml of reconstituted extract (<333 ug/ml), it is estimated that less than 2.9 parts of this substance in 10,000 parts of formulation penetrated the skin in this experiment and entered the reservoirs.

TABLE XIII

| Sample No. | Amount of 35A Cyclic 700 Added to Skin, mg. | Amount of 35A Cyclic 700 Found in Extract, ug | Percent of 35A Cyclic 700 Recovered |
|---|---|---|---|
| 1 | 1215 | <333 | <0.027 |
| 2 | 1114 | " | <0.030 |
| 3 | 1215 | " | <0.027 |
| 4 | 1114 | " | <0.030 |
| Mean | 1165 | <333 | <0.029 |

The above discussion of this invention is directed primarily to preferred embodiments and practices thereof. It will be readily apparent to those skilled in the art that further changes and modifications in the actual implementation of the concepts described herein can readily be made without departing from the spirit and scope of the invention as defined by the following claims.

What is claimed is:

1. A method of moisturizing skin, comprising applying to skin surface a composition containing (a) a locally administrable topical composition containing a topical carrier; and
(b) a hydroxy-terminated urethane compound having the formula:

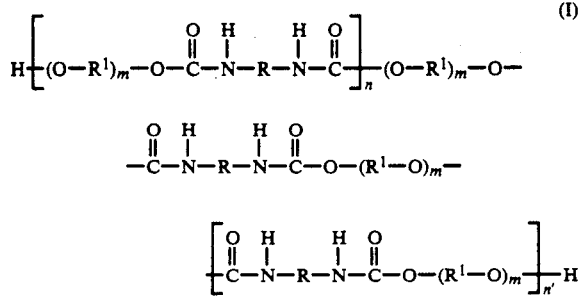

wherein:

R is an alkylene or alkenylene radical containing from one to about 20 carbon atoms; or a cycloalkylene or cycloalkenylene radical containing from about 5 to about carbon atoms, or a mononuclear or fused ring arylene radical containing from about 6 to about 10 carbon atoms, unsubstituted or substituted with one or more lower alkyl, lower alkoxy, lower alkoxy-substituted lower alkyl, nitro or amino groups or halogen atoms;

$R^1$ is the same or different alkylene or alkenylene radical;

m is an integer selected so as to provide an $(O-R^1)$ moiety having a molecular weight of from about 40 to about 6,000; and n and n' are the same or a different integer of from 0 to 30, inclusive, correlated with m so as to provide a hydroxy-terminated urethane compound having a molecular weight of from about 220 to about 200,000.

2. The method of claim 1, wherein each of n and n' is 0.

3. The method of claim 1, wherein m is an integer selected so as to provide an $+O-R^1+$ moity having a molecular weight of from about 40 to about 6000, correlated with n and n' so as to provide a hydroxy-terminated urethane compound having a molecular weight of from about 220 to about 37,000.

4. The method of claim 1, wherein m is an integer selected so as to provide an $+O-R^1+$ moity having a molecular weight of from about 400 to about 2000, correlated with n and n' so as to provide a hydroxy-terminated urethane compound having a molecular weight of from about 1000 to about 15,000.

5. The method of claim 1, wherein the topical carrier comprises a liquid or nonliquid carrier, a gel, a cream, an ointment, a lotion, an aerosol or an emulsifier.

6. The method of claim 5, wherein the locally administrable topical composition comprises a cosmetic, a sunscreen or an insect repellant.

7. The method of claim 6, wherein the hydroxy-terminated urethane compound is present in an amount of from about 3 wt.% to about 90 wt.% of the composition.

8. The method of claim 6 wherein the hydroxy-terminated urethane compound is present in an amount of from about 10 wt.% to about 25 wt.% of the composition.

* * * * *

UNITED STATES PATENT AND TRADEMARK OFFICE
CERTIFICATE OF CORRECTION

PATENT NO.    :    5,051,260
DATED         :    September 24, 1991
INVENTOR(S)   :    Samuel Chess et al.

It is certified that error appears in the above-identified patent and that said Letters Patent is hereby corrected as shown below:

Cover Page of Patent:    replace "[54] METHOD AND COMPOSITION FOR ENHANCING THE CUTANEOUS PENETRATION OF PHARMACOLOGICALLY ACTIVE AGENTS"
                         with --[54] METHOD AND COMPOSITIONS FOR ENHANCING THE CUTANEOUS PENETRATION OF PHARMACOLOGICALLY ACTIVE AGENTS--

Cover Page of Patent:    replace "[21] Appl. No.: 556,982"
                         with --[21] Appl. No.: 566,982--

Column 21, line 23, in Claim 1:    insert --10-- after "about"

Column 22, line 20, in Claim 5:    replace "1" with --4--

Signed and Sealed this

Fifth Day of January, 1993

Attest:

DOUGLAS B. COMER

*Attesting Officer*    Acting Commissioner of Patents and Trademarks

UNITED STATES PATENT AND TRADEMARK OFFICE
CERTIFICATE OF CORRECTION

PATENT NO. : 5,051,260
DATED : September 24, 1991
INVENTOR(S) : Chess, et al.

It is certified that error appears in the above-indentified patent and that said Letters Patent is hereby corrected as shown below:

Column 3, line 14, column 6, line 3, "about 10 carbon atoms" should read --about 13 carbon atoms--.

Claim 1, column 21, line 23, "to about carbon atoms" should read-- to about 13 carbon atoms--.

Signed and Sealed this

Seventh Day of June, 1994

Attest:

BRUCE LEHMAN

*Attesting Officer*  *Commissioner of Patents and Trademarks*